United States Patent [19]
Robertson et al.

[11] 3,934,646
[45] Jan. 27, 1976

[54] CONSTANT TEMPERATURE COLD-END CORROSION PROBE

[75] Inventors: Reed S. Robertson, Glen Ellyn; William R. Watson, Oaklawn, both of Ill.

[73] Assignee: Nalco Chemical Company, Chicago, Ill.

[22] Filed: Oct. 10, 1974

[21] Appl. No.: 513,870

Related U.S. Application Data

[62] Division of Ser. No. 384,072, July 30, 1973, Pat. No. 3,861,876.

[52] U.S. Cl................... 165/105; 23/230 C; 73/15 R
[51] Int. Cl.² .......................................... F28D 15/00
[58] Field of Search ........ 165/105; 23/230 C, 253 C; 73/15 R, 86

[56] References Cited
UNITED STATES PATENTS

| | | | |
|---|---|---|---|
| 1,711,804 | 5/1929 | Munters............................ | 165/105 |
| 2,834,858 | 5/1958 | Schaschl............................ | 23/230 C |
| 2,972,248 | 2/1961 | Gerhardt............................ | 23/230 C |
| 3,131,029 | 4/1964 | Dieman............................. | 23/230 C |
| 3,259,461 | 7/1966 | Griffin............................... | 23/230 C |
| 3,639,876 | 2/1972 | Wilson.............................. | 23/230 C |
| 3,801,467 | 4/1974 | Nobe................................. | 73/15 R |
| 3,861,876 | 1/1975 | Robertson......................... | 23/230 C |
| 3,869,912 | 3/1975 | Horvath............................. | 73/15 R |
| 3,871,444 | 3/1975 | Houser.............................. | 73/15 R |
| 3,875,794 | 4/1975 | Horvath............................. | 73/15 R |

*Primary Examiner*—Albert W. Davis, Jr.
*Assistant Examiner*—Daniel J. O'Connor
*Attorney, Agent, or Firm*—Lockwood, Dewey, Zickert & Alex

[57] ABSTRACT

Method and apparatus for determining the corrosion or acid deposition rate in the cold end of a boiler system, including a probe loop having an organic solvent circulating through the loop with a predetermined boiling temperature wherein the loop includes a removable specimen that can be tested for acid deposition or corrosion rate. Recirculation of the organic solvent maintains the surface temperature of the specimen within close limits approximating the maximum corrosion temperature.

2 Claims, 7 Drawing Figures

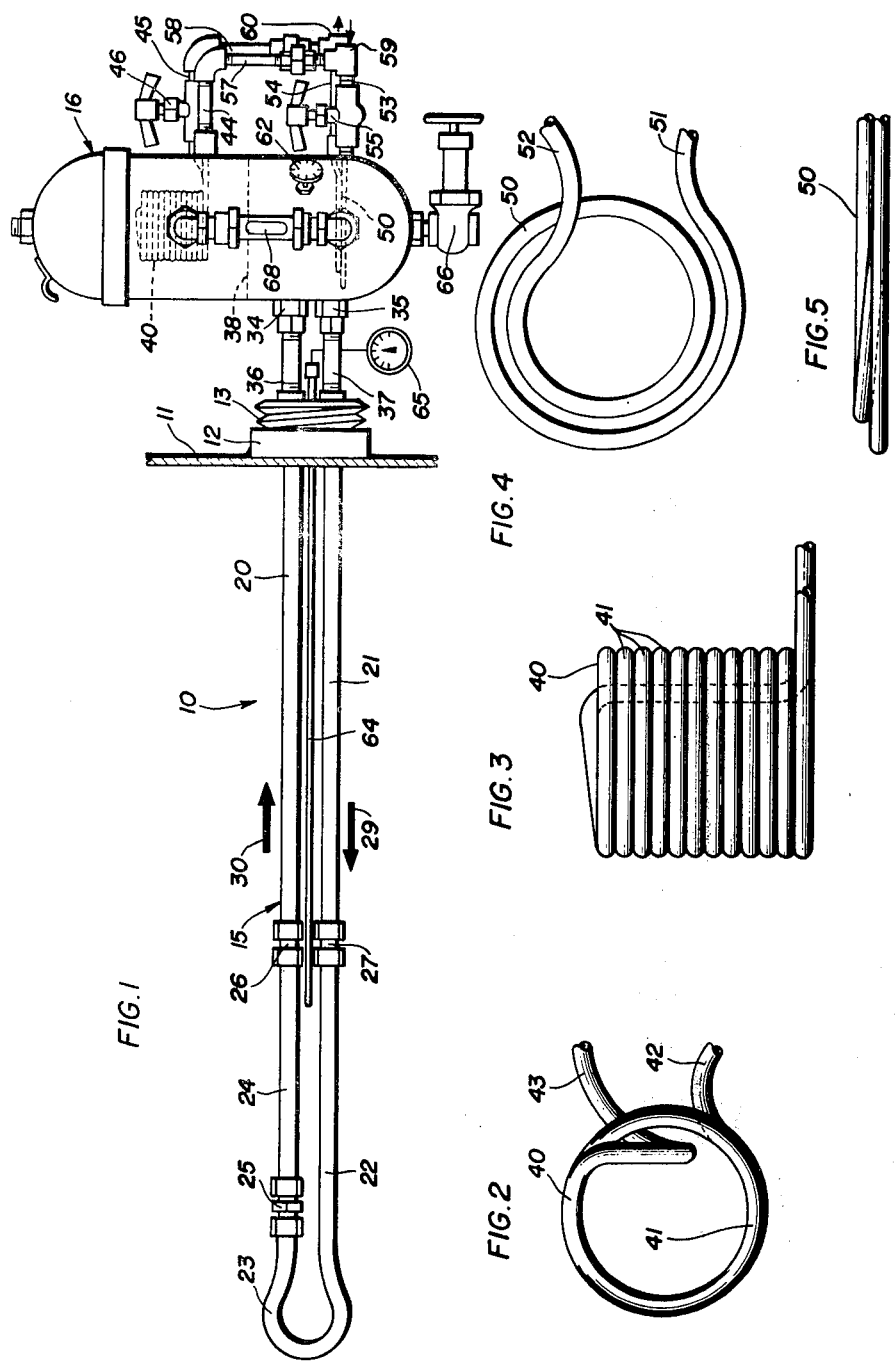

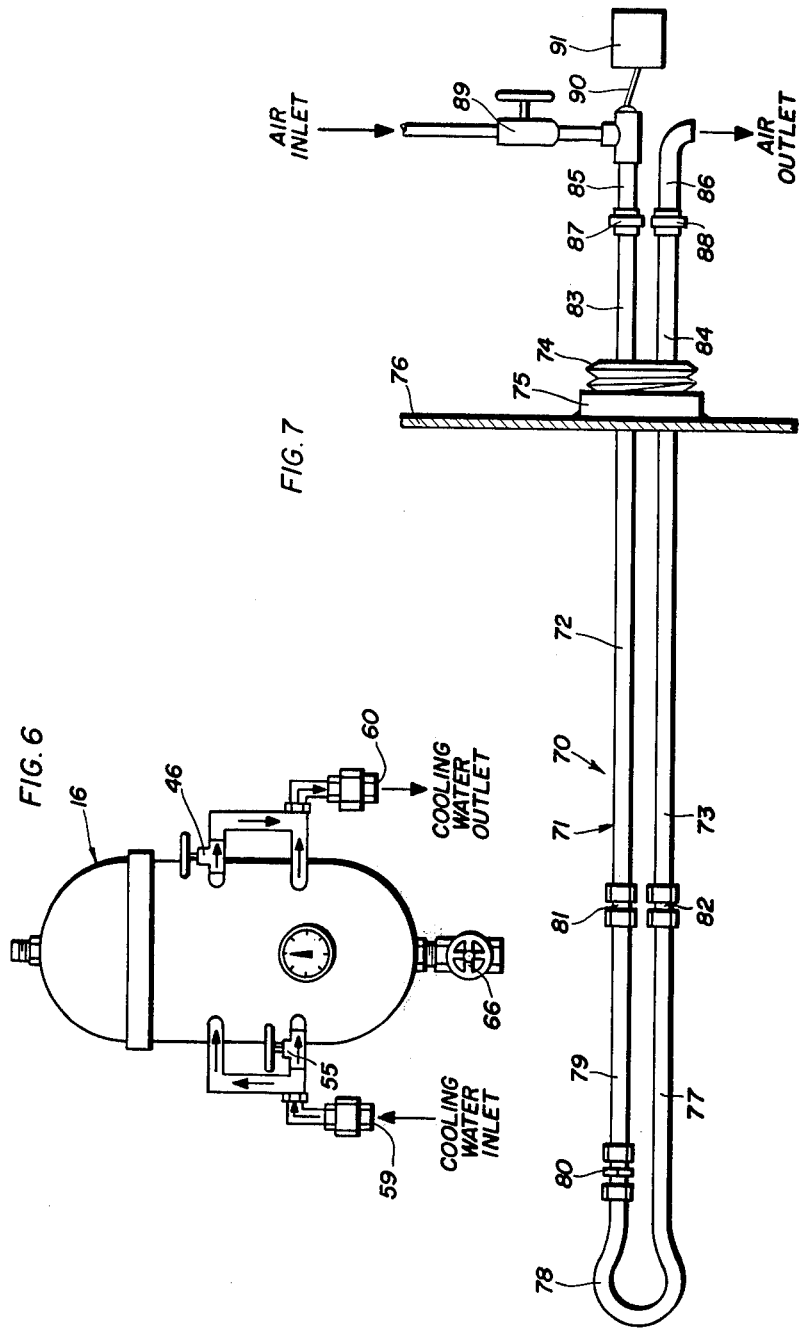

CONSTANT TEMPERATURE COLD-END CORROSION PROBE

This is a division of application Ser. No. 384,072, filed July 30, 1973, now U.S. Pat. No. 3,861,876.

This invention relates in general to a method and apparatus for measuring the acid deposition rate on metals and the corrosion rate of metals in the cold end of a boiler, and more particularly to a constant temperature cold-end corrosion probe for measuring the sulphuric acid corrosion rate of a flue gas stream of a boiler burning sulphur-containing fuel.

A major problem associated with burning residual fuel oil in boilers wherein the fuel oil contains sulphur concerns the corrosion of metal parts in the air heaters and economizers at the cold end of a boiler system wherein the corrosion is caused by the condensation of sulphuric acid from the flue gases onto metal surfaces of the air heaters or economizers at or below the acid dew point. Corrosion can be controlled through the use of fuel oil additives by reducing the amount of free acid formed, thereby lowering the acid dew point. An example of such a fuel oil additive is one called Nalco FIRE-SIDE 7250 made by Nalco Chemical Company of Chicago, Illinois. Other remedies also may be employed for controlling sulphuric acid corrosion.

Heretofore, it has been well known to determine the degree of beneficial effect of a cold-end corrosion control treatment after a boiler has been shut down.

It has also been heretofore proposed to utilize a constant temperature corrosion probe for determining flue gas corrosion in a boiler system by liquid cooling a probe in a wet-leg assembly, as explained in the article written by R. W. Kear, appearing in the *Journal of the Institute of Fuel* (1959), pages 267–273. Difficulties encountered in this system include complexity of the probe assembly, limited circulation and temperature control, and the inability to conveniently obtain both acid deposition rate and corrosion rate at the same point within the gas stream.

The constant temperature cold-end temperature probe of the present invention overcomes the problems heretofore known in determining useful acid deposition and corrosion rates for establishing an efficient and meaningful corrosion treatment program for a boiler system to enhance the life of the cold-end equipment. The probe includes a pipe loop mountable in the flue gas stream and connected to a tank containing an organic solvent that will boil at the desired operating temperature of the pipe loop. A corrosion coupon or specimen is removably mounted in the pipe loop and continually cooled by the recirculation of the organic solvent from the tank. A water cooled cooling coil and a water cooled condensing coil in the tank maintains the temperature of the solvent below that of the boiling temperature to produce the necessary circulation so that the corrosion specimen is continually being maintained at a constant temperature. The acid deposition rate can be established by connecting the pipe loop to a source of cooling air and utilizing a satisfactory specimen, it being appreciated that the acid deposition rate is measured at the same location in the system as where the corrosion rate may be measured.

It is therefore an object of the present invention to provide a new and improved method and apparatus for determining the corrosion rate of metals in the cold end of a boiler system during boiler operation to evaluate the corrosion control treatment program.

Another object of the present invention is in the provision of determining the corrosion rate of a metal in a boiler system through the use of cooled corrosion coupons maintained at a constant corroding temperature so that desired chemical treatment controlling cold-end corrosion can be ascertained.

A still further object of this invention resides in the provision of an apparatus for cooling a corrosion specimen in a boiler system for measuring corrosion rate which is simple in construction and reliable and which utilizes a solvent liquid-vapor loop within a flue gas stream having efficient and reliable temperature control.

A further object of this invention is in the provision of a method and apparatus for determining corrosivity of a flue gas stream in a boiler system which is capable of obtaining both acid deposition rate and corrosion rate at the same point within the flue gas stream.

A further object of this invention resides in the provision of a constant temperature cold-end corrosion probe for measuring corrosion in the flue gas stream of a boiler system which is generally self-contained and utilizes only a source of cooling water in the form of the usual tap water for effective operation.

A still further object of this invention is in the provision of a method and apparatus for inducing corrosion at one point in the flue gas stream of a boiler system by maintaining a corrosion specimen at a predetermined temperature in order to measure the corrosion that will take place downstream when the temperature reaches the predetermined temperature, thereby enhancing the evaluation of a corrosion control program.

Other objects, features and advantages of the invention will be apparent from the following detailed disclosure, taken in conjunction with the accompanying sheets of drawings, wherein like reference numerals refer to like parts, in which:

FIG. 1 is an elevational view of the constant temperature cold-end corrosion probe according to the invention;

FIG. 2 is a top plan view of the condensing coil removed from the coolant tank of the probe assembly;

FIG. 3 is a side elevational view of the condensing coil of FIG. 2;

FIG. 4 is a top plan view of the cooling coil removed from the coolant tank of the probe assembly;

FIG. 5 is a side elevational view of the cooling coil of FIG. 4;

FIG. 6 is a somewhat diagrammatic view of the coolant tank to illustrate the flow of cooling water through the tank; and FIG. 7 is a view similar to FIG. 1, but showing the probe assembly as connected to a source of cooling air for the purpose of measuring acid deposition rate.

The constant temperature cold-end corrosion probe of the invention is adapted to be installed in the flue gas stream where the temperature of the flue gas is preferably 300° F. or higher but less than about 650° F., this range of temperature being above the dew point temperature of the sulphuric acid or above the maximum corrosion temperature. The probe is cooled to a temperature below the dew point and where maximum corrosion usually occurs, such as about 250° F. for sulphuric acid. The probe is adapted to be operated to maintain a corrosion coupon on specimen at a constant temperature of about 250° F. for the duration of the test period.

A suitable hydrocarbon or organic solvent having a boiling temperature of about that which the coupon is to be cooled is recirculated through the coupon to maintain the surface temperature of the coupon within close limits. For example, where the maximum corrosion temperature is about 250° F., tetrachloroethylene (perchloroethylene) is recirculated through the probe to cool the specimen. The solvent is recirculated by cooling it in a tank outside of the flue gas stream to a temperature slightly below the boiling temperature. It has been established that a time period ranging from 20 to 30 days is optimum for obtaining representative corrosion rates in most boiler systems. However, it should be appreciated that the time period range of from 10 to 40 days may be employed, depending upon the boiler characteristics and program objectives. At the conclusion of the test period, the specimen is weighed to determine the corrosion rate. Operation of the probe is automatic, only requiring the need for cooling water at the coolant tank. Accordingly, the probe provides a reliable method of indicating the rate of sulphuric acid corrosion in the cold end of boilers. However, it should also be appreciated that the probe may be used to obtain other types of corrosion rates in the cold end of boilers.

Moreover, it should be appreciated that the boiler system need not be shut down when evaluating a corrosion control treatment program, as the probe of the invention may easily be removed after a test period to measure the corrosion rate of the coupon.

Referring now to the drawings, and particularly to FIG. 1, the probe assembly of the invention, generally designated by the numeral 10, is illustrated as being mounted in a breeching wall 11 of a boiler system and preferably between the economizer and preheater, although it may be mounted at any place in the flue gas stream on the fireside of the boiler where the temperatures desired to be encountered are present. Particularly, the temperature must be above the dew point of the corroding agent or above the maximum corroding temperature so that the probe which includes a coupon or specimen can be cooled to a temperature below the acid dew point or at a temperature where maximum corrosion exists. A female fitting 12 of a pipe coupling is suitably welded into the breeching wall 11 to receive a male fitting or plug 13 of the pipe coupling which supports the probe assembly. The probe assembly includes a pipe loop 15 extending from the male fitting 13 and within the boiler system exposed to the flue gas stream, and a coolant tank 16 extending from the male fitting 13 and arranged outside of the flue gas stream. The coolant is circulated through the pipe loop 15 and cooled in the tank 16.

The pipe loop 15 includes upper and lower pipe sections 20 and 21 of substantially the same length and which extend from the male fitting 13, an outer pipe section 22 having a loop 23, and a corrosion specimen or coupon 24. Suitable pipe couplings 25 and 26 are provided between the ends of the corrosion coupon 24 and the outer pipe section 22 and the inner pipe section 20, while a suitable coupling 27 is provided between the inner pipe section 21 and the outer pipe section 22. Accordingly, when removing the corrosion coupon 24 from the pipe loop 15, it can easily be accomplished by loosening the pipe couplings 25, 26 and 27 in order to remove the coupon and process it for corrosion data.

Similarly, the coupon can be replaced or a new coupon can be inserted by manipulation of the couplings 25, 26 and 27. It should be noted in FIG. 1 that the coupon is arranged adjacent the loop end of the probe so that the coupon is spaced from the breeching wall 11 and will be in a more direct position relative to the flue gas stream. Preferably, the specimen should be in the center of the stream. The pipe loop 15 is positioned so that the upper and lower runs or sections are arranged in a vertical plane. The coolant is recirculated through the pipe loop by flowing outwardly to the loop along the lower pipe section and returning to the tank through the upper pipe section as indicated by the arrows 29 and 30. Moreover, it should be appreciated that the corrosion specimen 24 should be at the top as shown in FIG. 1.

The coolant tank 16 is provided with upper and lower ports 34 and 35 for connection to upper and lower short pipe sections 36 and 37 which are in turn connected to the male pipe fitting 13. The ports 34 and 35 are adjacent the lower end of the tank and the coolant level represented by the dotted line 38 is above the upper port 34. A vapor coil or condensing coil 40 is suitably supported above the coolant level 38 within the coolant tank 16, functioning to extract most of the heat from the coolant and to convert the gas phase back to liquid phase. As shown in FIGS. 2 and 3, the condensing coil 40 includes a plurality of superposed coil turns 41 having inlet and outlet ends 42 and 43 suitably connected to inlet and outlet water pipes 44 and 45. A condenser coil control valve 46 is provided in the outlet pipe to control the flow of cold water through the condensing coil 40 and the degree of cooling action desired. The majority of the heat removed from the coolant is removed by the condensing coil 40.

A liquid phase tempering coil 50 is also mounted within the coolant tank and at a level below the coolant level so that it is always within the liquid phase. The coil 50 includes inlet and outlet ends 51 and 52 which are connected to inlet and outlet water pipes 53 and 54. A cooling coil controlling valve 55 controls the cold water flow through the cooling or tempering coil 50 and degree of cooling action desired. The inlet water pipes 44 and 53 are connected by a common pipe section 57, while the outlet water pipes 45 and 54 are connected by a common water pipe section 58. Similarly, an inlet 59 is provided for the common water pipe section 57 while an outlet 60 is provided for the common water section 58. The inlet 59 is connected to a suitable source of cold water while the outlet 60 is connected to a suitable drain. Accordingly, cold water is supplied to the coils 40 and 50 in order to provide a suitable cooling of the coolant during operation of the probe. A temperature gauge 62 is provided to register the temperature of the coolant within the tank, and as already indicated, it is preferable that the coolant in the tank be at least 15, and possibly as much as 50, degrees less than the boiling temperature of the coolant in order to assist in circulation of the coolant through the probe loop. Accordingly, the cold water supply would be adjusted with the control valves 46 and 55 in order to obtain the desired temperature of the coolant within the tank. For purposes of registering the temperature of the flue gas within the stream, a thermocouple 64 is provided between the upper and lower sections of the probe loop and extending from the male fitting 13. A suitable connection is provided at the outside of the furnace wall to connect the thermocouple to a temperature gauge 65. A drain valve 66 is provided at the bottom of the coolant tank 16 for draining the coolant from the tank when desired.

The corrosion specimen and coupon 24 would be of a suitable metal equivalent to that which is desired to obtain corrosion data information for evaluating the corrosion treatment program. For example, in the event that it is desired to determine what corrosion rate there would be for sulphuric acid in the flue gases, it would be preferable that the corrosion specimen be of a mild steel, such as 1010 to 1020. Where it is desired to determine the rate of sulphuric acid corrosion in the cold end of the boiler, and since it is known that maximum sulphuric acid corrosion usually occurs at about 250° F., the constant temperature cold-end corrosion probe of the invention is set up to operate with a corrosion coupon of mild steel and to be maintained at a constant temperature of 250° F. for the duration of the test period. While the corrosion specimen is of the type of metal subjected to corrosion, the remaining part of the pipe or probe loop is preferably of stainless steel. In this instance, the organic solvent used as a coolant would preferably be one having a boiling point of 250° F., such as tetrachloroethylene, which when recirculating will maintain the surface temperature of the corrosion specimen within close limits at this temperature. The solvent recirculates, thereby acting as a coolant because the density of the boiling liquid in the probe loop 15 is less than the density of the cooler liquid in the tank 16. This difference creates a natural gravity flow through the probe. The temperature of the solvent within the tank is maintained at about 15° to 50° less than the boiling temperature of the coolant by adjustment of the cold water supply. Thereafter, the probe operates automatically. It can be appreciated that from time to time it is advisable to check the level of the coolant in the tank by viewing the sight glass 68 and maintaining the level of liquid coolant above the upper port 34 and also below the condensing coil 40. At the conclusion of the test period, the probe assembly can be removed from its mounting, so that the corrosion specimen may be disassembled from the probe loop, processed and suitably weighed to determine the corrosion rate for the test period. By knowing the corrosion rate, suitable remedies can be taken for reducing corrosion such as providing certain fuel oil additives for the fuel.

It can therefore be appreciated that the probe assembly provides a method of cooling a corrosion specimen where the specimen is exposed to a flue gas stream. The probe assembly cools the specimen to a predetermined temperature lower than that of the gas stream and at the maximum corrosion rate for the specimen. The method includes connecting the opposite ends of the corrosion specimen to vertically spaced upper and lower ports in the coolant tank which is located outside the flue gas stream and wherein a supply of liquid coolant is provided. Thereafter, the liquid coolant in the tank is subjected to a cooling action and maintained at a temperature lower than the boiling point of the coolant so that recirculation of the coolant through the corrosion specimen can be accomplished, and the corrosion specimen can be continually cooled and maintained at the maximum corrosion temperature.

When fully evaluating a corrosion treatment program, an acid deposition rate is first established by use of the probe assembly 70 shown in FIG. 7 which differs from the probe assembly 10 of FIG. 1 only in that the probe loop is cooled by compressed air instead of a liquid coolant. The probe assembly includes upper and lower pipe section 72 and 73 extending from the pipe plug 74 mounted in the pipe fitting 75 of the breeching wall 76, an outer pipe section 77 having a loop 78 and a specimen or coupon 79 interconnected between the upper section 72 and the outer section 77 by suitable couplings 80 and 81. A coupling 82 is provided between the lower section 73 and the outer section 77. The upper and lower pipe sections 72 and 73 are connected through the pipe plug 74 to outer upper and lower sections 83 and 84, which are in turn connected to an air inlet pipe section 85 and an air outlet pipe section 86 through pipe couplings or unions 87 and 88. Air flow through the probe loop 71, and therefore the temperature of the loop, is controlled by the air inlet valve 89. Thermocouple conductors 90 are connected through the air inlet pipe to a thermocouple at the inside of the specimen 79 for measuring the skin temperature of the specimen. The conductors are also connected to a pyrometer 91 for registering the temperature.

The specimen 79 in this embodiment is of stainless steel. The time period for leaving the specimen subjected to the flue gases is less than that for a corrosion rate test by operating the specimen at various temperatures and taking measurements of acid deposition rate. The temperature where maximum deposition occurs can be determined and that is the same temperature where maximum corrosion is likely to occur so that the correct temperature for operating the corrosion testing probe of FIG. 1 is then determined. After running the specimen 79 for a time period, it is removed and the acid content per unit time for that temperature may be measured analytically by titration of the water wash-off of the acid. The acidity and sulphate content of the wash-off is measured analytically by any suitable means such as by titration, colormetric or other method.

Accordingly, it can be appreciated that the present invention provides a method and apparatus for inducing corrosion at a point in the flue gas stream by maintaining a specimen at a constant temperature where maximum corrosion occurs, thereby determining what corrosion will occur downstream when the temperature reaches the temperature of the specimen. Accordingly, the corrosion rate of the metal of concern is measured in order to determine what remedy can be utilized for reducing or minimizing corrosion and thereby enhancing the life of the cold end of the boiling system.

It will be understood that modifications and variations may be effected without departing from the scope of the novel concepts of the present invention, but it is understood that this application is to be limited only by the scope of the appended claims.

The invention is hereby claimed as follows:

1. Apparatus for cooling a tubular metal corrosion specimen and maintaining the specimen at a predetermined temperature where the specimen is exposed to a gas stream temperature above said predetermined temperature, said apparatus comprising a tank mounted outside the gas stream having a liquid coolant supply therein which has a boiling point substantially the same as said predetermined temperature, vertically spaced upper and lower ports in said tank, the level of liquid coolant being above the upper port, piping connecting the opposite ends of said tubular specimen to said ports thereby defining a probe loop, a cooling coil in said tank substantially at the level of the lower port, a condensing coil in the tank positioned above the level of the liquid, means connecting said coils to a cold water supply, and valve means for each coil controlling the flow of water therethrough to regulate the temperature of the coolant.

2. The combination as defined in claim 1, wherein said probe loop is vertically positioned with the specimen in the upper part of the loop.

* * * * *